(12) United States Patent
Utas et al.

(10) Patent No.: US 10,974,025 B2
(45) Date of Patent: Apr. 13, 2021

(54) URINARY CATHETER WITH VARYING PROPERTIES

(71) Applicant: DENTSPLY IH AB, Mölndal (SE)

(72) Inventors: Jan Utas, Kungsbacka (SE); Niklas Dahlberg, Lerum (SE); Martin Lovmar, Mölndal (SE)

(73) Assignee: DENTSPLY IH AB, Mölndal (SE)

( * ) Notice: Subject to any disclaimer, the term of this patent is extended or adjusted under 35 U.S.C. 154(b) by 657 days.

(21) Appl. No.: 15/635,940

(22) Filed: Jun. 28, 2017

(65) Prior Publication Data

US 2018/0001055 A1    Jan. 4, 2018

(30) Foreign Application Priority Data

Jun. 30, 2016  (EP) ..................... 16177066

(51) Int. Cl.
*A61M 25/00* (2006.01)
*B29C 48/21* (2019.01)
(Continued)

(52) U.S. Cl.
CPC ....... *A61M 25/0054* (2013.01); *A61L 29/041* (2013.01); *A61L 29/085* (2013.01);
(Continued)

(58) Field of Classification Search
CPC ...... A61L 29/041; A61L 29/085; A61L 29/14; A61M 25/0009; A61M 25/0017;
(Continued)

(56) References Cited

U.S. PATENT DOCUMENTS

| 4,250,072 A | 2/1981 | Flynn |
| 5,533,985 A * | 7/1996 | Wang ................ A61M 25/0009 604/264 |

(Continued)

FOREIGN PATENT DOCUMENTS

| DE | 4032869 A1 | 4/1992 |
| JP | H09512445 A | 12/1997 |

(Continued)

OTHER PUBLICATIONS

European Search Report for European Patent Application No. 16177066.4, dated Jan. 3, 2017 (8 pages).

(Continued)

*Primary Examiner* — Benjamin J Klein
(74) *Attorney, Agent, or Firm* — Perkins Coie LLP (57) ABSTRACT

A urinary catheter and a method of its manufacture are disclosed. The urinary catheter comprises a tubular shaft extending between an insertion end and a discharge end, the tubular shaft being formed of at least two materials having different properties. The materials are arranged substantially separated from each other in distinct zones, wherein at least one of the width and thickness of said zones varies over the length of the tubular shaft, to form two or more uniform sections of the tubular shaft having various relative amounts of said materials, and wherein at least one transition between two such uniform sections is formed by at least one transition section providing a gradual transition between the uniform sections. The catheter can e.g. be produced by intermittent extrusion.

20 Claims, 6 Drawing Sheets

(51) Int. Cl.
  *A61L 29/04* (2006.01)
  *A61L 29/08* (2006.01)
  *A61L 29/14* (2006.01)
  *B29K 21/00* (2006.01)
  *B29K 75/00* (2006.01)
  *B29L 31/00* (2006.01)

(52) U.S. Cl.
  CPC ......... *A61L 29/14* (2013.01); *A61M 25/0009* (2013.01); *A61M 25/0017* (2013.01); *A61M 25/0045* (2013.01); *A61M 25/0053* (2013.01); *B29C 48/21* (2019.02); *A61M 2025/0008* (2013.01); *A61M 2025/0046* (2013.01); *B29K 2021/003* (2013.01); *B29K 2075/00* (2013.01); *B29K 2995/0092* (2013.01); *B29L 2031/7542* (2013.01)

(58) Field of Classification Search
  CPC .......... A61M 25/0045; A61M 25/0053; A61M 25/0054; A61M 2025/0008; A61M 2025/0046
  See application file for complete search history.

(56) References Cited

U.S. PATENT DOCUMENTS

| | | | |
|---|---|---|---|
| 5,599,326 A | * | 2/1997 | Carter .............. A61M 25/0045 604/524 |
| 5,622,665 A | | 4/1997 | Wang |
| 5,951,929 A | | 9/1999 | Wilson |
| 2011/0288532 A1 | | 11/2011 | Faherty et al. |
| 2015/0297862 A1 | | 10/2015 | Sadik et al. |

FOREIGN PATENT DOCUMENTS

| | | |
|---|---|---|
| JP | 2001218833 A | 8/2001 |
| JP | 2011250903 A | 12/2011 |
| WO | 0236194 | 5/2002 |
| WO | 2014077881 | 5/2014 |

OTHER PUBLICATIONS

Communication pursuant to Article 94(3) EPC dated May 6, 2020 for European Patent Application No. 16177066.4 (4 pages).
Office Action dated Feb. 9, 2021 for Japanese Patent Application No. 2018-568220 (11 pages).

* cited by examiner

URINARY CATHETER WITH VARYING PROPERTIES

CROSS-REFERENCE TO RELATED APPLICATIONS

This patent document claims priority of European Patent Convention Application No. 16177066.4, entitled "URINARY CATHETER WITH VARYING PROPERTIES" and filed on Jun. 30, 2016, which is incorporated herein by reference in its entirety.

FIELD OF THE INVENTION

The present invention is related to a urinary catheter. The invention is also related to a corresponding method of manufacture.

BACKGROUND OF THE INVENTION

Urinary catheters are commonly used for draining urine from the bladder. One type of urinary catheters is indwelling catheters, so-called Foley catheters, which are maintained in place in the urethra for an extended period of time, such as for days, weeks or even months. Another type of urinary catheters is intended for short term use, so-called intermittent catheters. Intermittent urinary catheters are used for draining the bladder once, and then be removed. Intermittent catheters are typically used for a few minutes, and catheterization is typically made by the user him/her self, so-called self-catheterization, and is typically performed many times a day. Typically catheters for intermittent catheterization are used by patients suffering from urinary incontinence, urinary retention or neurogenic bladder dysfunction. Many of the users using self-catheterization have limited or reduced dexterity. Using an intermittent catheter, the bladder may be drained through a natural or artificial urinary canal. Many catheters for intermittent catheterization are provided with a hydrophilic coating or the like, providing a smooth and slippery surface when wetted, for safe and comfortable insertion in the urinary canal.

However, catheterization, and in particular for male users, can often be complicated. The male urethra is long (typically 15-29 cm), and comprise a number of curves and restricted areas through which it may be difficult to insert a catheter. On the one hand, it is generally a desire to make the catheter as stiff and rigid as possible, since this makes it easier to push and control/manipulate the catheter from the rear end during insertion. A stiff catheter will also resist kinking, buckling and other deformations. However, a stiff catheter will have difficulty in finding its way and navigating around the narrow and restricted passages in the urethra, and may also cause pain and injury to the user. Thus, from this point of view, the catheter should instead be made as soft as possible. The solution to this problem has so far been to use a compromise, i.e. to use catheters which are neither soft nor stiff, and which are not optimal from the point of maneuverability and also not optimal in view of reducing pain, discomfort and injury on the user or patient.

There have been some proposals to use urinary catheters having varying properties over the length. For example, WO 2014/077881 discloses a urinary catheter in which sections or zones are made more flexible than other sections/zones, by providing cutouts and the like in these sections. However, this proposed catheter is still far from optimal from a use perspective, and also very difficult and costly to produce.

There is therefore a need for a urinary catheter which at least partly alleviates the above-discussed problems. In particular, there is a need for a new urinary catheter having improved flexibility/rigidity characteristics, and improved usability, and which is more cost-efficient to produce.

SUMMARY OF THE INVENTION

It is therefore an object of the present invention to provide an improved urinary catheter, as well as a corresponding method for manufacturing such an improved urinary catheter.

This object is achieved with a method and a urinary catheter according to the appended claims.

According to a first aspect of the present invention, there is provided a urinary catheter comprising a tubular shaft extending between an insertion end a discharge end, the tubular shaft being formed of at least two materials having different properties, each of said materials being arranged substantially separated from each other in distinct zones, at least one of said distinct zones preferably extending over essentially the entire length of the tubular shaft, wherein at least one of the width and thickness of said zones varies over the length of the tubular shaft, to form two or more uniform sections of the tubular shaft having various relative amounts of said materials, and wherein at least one transition between two such uniform sections is formed by at least one transition section providing a gradual transition between said uniform sections.

The at least one property differing between the at least two materials may be related to one or more of hardness, bending stiffness, tensile modulus, flexibility, elasticity and color. Preferably, the two materials differ at least in respect of hardness, measureable e.g. as Shore A or micro Shore A. In the context of the present invention, Shore A refers to hardness measurements made under the standard ASTM D2240-05, and micro Shore A (µShoreA) refers to hardness measurements made under the standard DIN ISO 7619. Micro Shore A can e.g. be measured by commercially available equipment, such as Bareiss Digi test II.

By arranging the two materials in zones having varying thickness and/or width, the tubular shaft is provided with varying properties along the length. More specifically, the tubular shaft is provided with two or more uniform sections having inherently uniform properties, but where the properties between such uniform sections differ. Thus, such uniform sections may e.g. have different hardness and/or flexibility.

Further, by arranging transition sections between said different uniform sections, there is a gradual transition between the width or thicknesses of the zones between said different uniform sections. Hereby, a very robust catheter is provided. The gradual transition reduces the risk of kinks, deformation, cracks and other deformation and/or distortion of the catheter tube. Hereby, a robust and reliable transition between the uniform sections is provided. It also prevents deformation of the catheter during production, packaging, storage and use. In addition, the transition section(s) makes the boundaries between the parts having different properties less distinct, which is very advantageous. For example, it makes the exact position of these boundaries of less importance and the catheter more versatile.

It has also been found that such catheters can be produced very cost-efficiently, e.g. by means of intermittent extrusion, as will be discussed in more detail below.

The discharge end is preferably formed as a flared rearward part, and the tubular part is preferably provided with an internal lumen extending between at least one drainage opening at or in the vicinity of the insertion end and an outlet opening at the discharge end. The insertion end preferably has a closed forward end. The discharge end may alternatively be provided with other connection interfaces, such as a luer connection. Such a connection interface is particularly of interest when the catheter is intended for administration of medicaments and the like.

The urinary catheter preferably has only one, single internal lumen extending between the outlet opening and drainage openings arranged close to the proximal, insertion end of the catheter.

One or several discharge openings may be arranged at or in the vicinity of the insertion end. In a preferred embodiment, the discharge openings are arranged in the side wall of the catheter, at some small distance from the insertion end. The insertion end, i.e. the tip of the catheter, is preferably closed, and is preferably formed in a rounded shape. However, alternatively or additionally, a drainage opening may also be formed in the tip.

The term "tubular shaft" as used herein refers to an object at least part of which forms a tube. The term "tube" here refers to an elongated shaft with a lumen therein. The tube may typically be an elongate hollow cylinder, but may also be a hollow shaft of other cross-sectional shapes.

The term "flared" here indicates a shape which expands or opens outwardly, so that the cross-sectional area at least in some parts increases in a direction away from the insertion end. The flared rearward end preferably has a circular cross-section, but may also have non-circular cross-sections, such as oval or elliptical cross-sections.

The urinary catheter is preferably a urinary catheter for intermittent catheterization, i.e. for short time use, such as catheterization of a few minutes duration, being repeated a number of times each day. The term "short term use" indicates a use that is limited in time, and in particular limited to a time period of less than 15 minutes, and preferably less than 10 minutes, and most preferably less than 5 minutes. The catheter of the present invention is excellently suited for self-catheterization, and can safely and easily be used also by inexperienced users, and/or users suffering from poor dexterity. The catheter is further preferably provided with a hydrophilic surface coating provided on at least an insertable part of the catheter. The hydrophilic surface coating exhibits a low friction when wetted with a wetting liquid, such as water or saline.

The urinary catheter is particularly suited for male catheters, preferably having a total length within the range of 35-40 cm, and having an insertable length within the range of 20-35 cm.

The tip may be straight, extending in the same direction as the tubular shaft and forming a rounded forward end, thereby forming a Nelaton type catheter. However, the tip may also be curved, forming a Tiemann or Coude type catheter. Tiemann and Coude catheters have a tip which is angled upward, to assist in negotiating the male prostatic curve. Thus, this tip form facilitates passage through the bladder neck in the presence of obstruction e.g. from a slightly enlarged prostate gland (e.g. in benign prostatic hyperplasia), and can be helpful for such and other difficult insertions.

The tip may be formed directly in the forward end of the tubular shaft, e.g. by melting. However, it is also possible to provide a separately manufactured tip, of the same or a different material, and subsequently attaching this tip to the forward end of the tubular shaft. Such a separately tip may be manufactured by injection molded, but may also be manufactured in other ways. A separately produced tip may be connected to the tubular shaft by at least one of welding, adhesion and injection molding.

Preferably, each of the one or more transition sections has an extension within the range of 2-30% of the total length of the tubular shaft, and more preferably within the range 4-20%, and most preferably within the range 5-10%.

Additionally or alternatively, each of the one or more transition sections preferably has an extension within the range of 0.5-10 cm, and more preferably within the range 1-5 cm, and most preferably within the range 2-4 cm.

Further, the two or more uniform sections in total preferably extend over at least 50% of the total length of the tubular shaft, and preferably at least 75%, and most preferably at least 90%.

In a preferred embodiment, the two materials have different hardness, one being softer and one being more rigid, thereby providing uniform sections having different flexibility.

The tubular shaft is preferably an extruded tube formed by intermittent extrusion using two or more materials.

The catheter tube preferably comprises a circular wall surrounding an inner lumen, and wherein the circular wall has a uniform and constant wall thickness around the circumference and over substantially the entire length of the tubular shaft. Similarly, the catheter tube preferably has a constant, or essentially constant, outer diameter along its entire length, as well as a constant, or essentially constant, inner diameter along its entire internal lumen.

Preferably, at least one of said distinct zones extend over essentially the entire length of the tubular shaft. In one embodiment, two or more distinct zones extend ofther entire length of the tubular shaft. In one embodiment both/all of said at least two distinct zones extend continuously over essentially the entire length of the tubular shaft. This means that the material of this zone is present at least to some extent at all cross-sections over the length of the tubular shaft. Providing one, and preferably both, the different materials continuously over the entire length enables very efficient manufacturing, in particular when intermittent extrusion is used.

In another line of embodiments, the distinct zones of different materials are extending in a longitudinal direction of the catheter, and being separated in layers, each layer preferably extending around the circumference of the catheter, the layers having varying thickness along the length of the catheter.

Thus, continuously or non-continuously extending zone(s) may e.g. be arranged as a layer with varying thickness, at all places extending around the entire circumference of the tubular shaft. This is of advantage since it enables the properties of this material to be present over the entire length and the entire circumference. For example, this material may be better suited than the other for use on the outer surface of the catheter, e.g. by having less friction, being smoother with less surface roughness, being easier to coat or the like, and in this way the entire surface can be made of this material.

In one line of embodiments, the distinct zones of different materials are extending in a longitudinal direction of the catheter, and being separated in a circumferential direction, the zones having varying width in the circumferential direction along the length of the catheter.

Thus, continuously or non-continuously extending zone may be arranged with varying width, so that it at least partly extends as a strip in the tubular shaft. The width may vary between a state where the width extends over the entire or close to the entire circumference, and a state where the width extends over only a limited or very limited part of the circumference, and any intermediate state there between. In this way, the properties of the catheter will, in addition to the variation between various parts and sections of the catheter along the length, also provide asymmetric and non-uniform properties around the catheter circumference. Hereby, the catheter shaft will have different properties in different rotational positions, such as e.g. being more flexible and easier to bend in one direction, such as a vertical direction, than in another, such as a horizontal direction. This is of great advantage, since it enables for the user to control the properties during insertion, e.g. by rotating the catheter. In case the two materials and the two zones are visibly discernible from each other, this may also function as a marker indicating the rotational position of the catheter, which is of advantage e.g. when the properties of the catheter differs between different direction, and also when a curved Tiemann/Coude tip is used. Alternatively or additionally, it may functions as markers indicating the length position along the catheter shaft. This is of advantage since it enables the user to know how far the catheter has been inserted into the urethra at all times during insertion. This is of advantage to control the catheterization more efficiently, e.g. by becoming aware of where certain difficult passages are situated, and manipulate the catheter more carefully through said passages.

The uniform sections having different properties, such as being relatively softer and relatively stiffer may be arranged in various ways, thereby fulfilling various needs.

In one embodiment, the tubular shaft comprises a uniform section being closest to the insertion end which is softer than another section being farther away from the insertion end. In one embodiment, the shaft only comprises these two uniform sections, and with a transition section there between. Each of said two sections preferably extends over at least 25% of the total length of the catheter shaft, and preferably over at least 40%, and most preferably over at least 45%. Thus, for a male catheter, typically having a catheter shaft being 30-40 cm long in total, the softer forward section may be 8-19 cm long, and preferably 12-18 cm, and the stiffer rearward section may have at least a similar length or be even longer. The transitional section preferably has a length in the range 0.5-10 cm, and preferably 1-5, and most preferably 2-4 cm. Making the catheter softer towards the insertion end and stiffer towards the discharge end is often advantageous. The softer part makes insertion easier, facilitating passage through restricted, curved or narrow areas of the urethra, making it possible for the catheter to find its own way through the urethra when being pushed inward, and without causing discomfort and pain to the user, and being gentle to the urethra. At the same time, the stiffer part towards the discharge end makes it easier for the user to manipulate/control the catheter during insertion, enabling the catheter to be efficiently pulled inward from behind, and avoiding kinking, buckling and other deformation of the catheter. Further, the transition section makes the transition between these different parts having different properties smooth and avoids problems in the transition area.

However, more than one softer uniform section and/or more than one stiffer uniform section may also be provided, and distributed in the longitudinal direction.

In one embodiment, the tubular shaft comprises at least four uniform sections, at least of two being relatively softer and at least two being relatively stiffer, the softer and stiffer sections being arranged in an alternating fashion along the length of the catheter shaft, and with transition sections being arranged between all adjacent uniform sections.

Preferably, the catheter shaft is predominantly made of stiffer uniform sections, and with softer uniform sections arranged where they are most needed. Preferably, stiffer uniform sections have extensions in the length direction being at least 2 times the length of any of the softer uniform sections, and preferably at least 3 times, and most preferably at least 4 times. For example, softer uniform sections may be arranged at or close to the insertion end and at or in the vicinity of the middle of the catheter shaft or the middle of an insertable part of the catheter shaft.

The male urethra generally comprises, seen from the tip of the penis—the external urethral meatus—and in the direction towards the bladder, four sections. A first section may be referred to the penile part. This part is relatively straight and uncomplicated from a catheter insertion point of view. Next, there is the bulbous part, which is separated from the penile part by suspensory ligament. This transition may sometimes be problematic in view of catheterization. After the bulbous part follows the membranous part, in which the urethra performs a sharp bend, and where the external sphincter, the urogenital diaphragm, is located. This part, which is relatively short (1-2 cm) is often the most difficult to pass for a catheter. Following the membranous part follows the prostatic part (sometimes subdivided into prostatic urethra and pre-prostatic urethra), which leads past the prostate and ends with the internal sphincter at the bladder neck. This part may for some users also be difficult to pass for a catheter. Thus, the softer uniform sections are preferably located at positions of the catheter shaft which correspond to the location of some or all of these difficult sections of the urethra for normal users, and when the catheter has been fully inserted. Thus, softer uniform sections may e.g. be arranged at locations corresponding to one or several of the suspensory ligament (i.e. the transition between the penile part and the bulbous part of the urethra), the external sphincter, i.e. at the membranous part of the urethra, in the area of the prostate, and at the internal sphincter. The other sections may be stiffer uniform sections. Further, the transition sections makes the exact positioning of these softer sections less sensitive, and also makes the catheters more versatile, and useable for a broad range of users, despite some variations in length of the urethra etc.

The words "soft"/"softer" and "stiff"/"stiffer" here means relatively more flexible and relatively more rigid, respectively. Thus, a soft/softer section has a lower Shore A or micro Shore A value, a lower bending stiffness and/or a lower tensile modulus than a stiff/stiffer section.

The softer and stiffer sections are formed by varying the amount of softer and stiffer materials of the two zones in said sections. Preferably, the stiffer sections comprises at least 60% by weight, and preferably at least 70%, and most preferably at least 80%, of the material of said two or more materials that is the stiffest, i.e. the material having highest hardness, highest bending moment and/or highest tensile modulus. The other material(s) are preferably present in an amount of 0-40%, and preferably in an amount of 0-30%, such as 0-25%, 0-20%, 0-15%, 5-30%, 5-25%, 5-20%, 5-15%, 10-30% or 10-20%. Correspondingly, the softer sections preferably comprises at least 60%, and preferably at least 70%, and most preferably at least 80%, of the material of said two or more materials that is the softest, i.e. the material having lowest hardness, lowest bending moment and/or lowest tensile modulus. The other material(s) are preferably present in an amount of 0-40%, and preferably in an amount of 0-30%, such as 0-25%, 0-20%, 0-15%, 5-30%, 5-25%, 5-20%, 5-15%, 10-30% or 10-20%.

In one embodiment, at least one of said uniform sections, being relatively softer, has a micro Shore A hardness in the range of 50-69, and another of said uniform sections, being relatively stiffer, has a micro Shore A hardness in the range of 70-100.

In one embodiment, at least one of said uniform sections, being relatively softer, has a bending stiffness in the range of 25-150 MPa*mm$^4$, and another of said uniform sections, being relatively stiffer, has a bending stiffness in the range of 180-1600 MPa*mm$^4$, and preferably 300-1500 MPa*mm$^4$. In particular, it has been found that these bending stiffness ranges are of great advantage for catheters of Charriere (Ch) sizes 12-16.

In one embodiment, at least one of said uniform sections, being relatively softer, has a tensile modulus in the range of 0.5-5 MPa, and preferably 2-5, and another of said uniform sections, being relatively stiffer, has a tensile modulus in the range of 10-50 MPa, and preferably 15-45 MPa.

It has been found that soft parts falling with at least one of said preferred ranges of hardness, bending stiffness and tensile modulus, and most preferably two or three of these are of particular advantage.

The softer uniform sections may also be used for allowing the catheter to be bent or curved during storage, allowing the catheter to be arranged in a package in a more compact way. Softer materials are easier to bend, and generally have less memory, thereby alleviating permanent deformation during storage, and allowing the catheter to unfold to a relatively straight disposition when being removed from the package even after a prolonged period of storage. Thus, provision of a softer uniform section in the middle of the catheter facilitates bending/folding of the catheter in this area, which may reduce the length of the package with 50% or more. Further softer uniform sections may also be provided and used to this end, enabling the catheter to be bent/folded more than once, to be arranged in a zigzag shape, a curled shape or the like.

By "material" is in the context of the present application meant a single material, formed by one or more chemically combined constituents, or blends or mixtures of constituents which are not chemically combined. By "different materials" is in the context of the present invention meant materials having different properties in terms of e.g. hardness, bending stiffness and/or tensile modulus. Such different materials may be formed by totally different constituents, by smaller or larger parts of the constituents being different, or by materials having the same constituents, but being provided with different properties by treatment, processing or the like.

Many different materials may be used in the tubular shaft for forming the two or more zones. The materials may each be a single material, or a mixture or blend of various materials. The materials may e.g. be thermoplastic elastomers, such as polyolefin based elastomers, or thermoplastic polymers, such as polyethylene, polypropylene or polyvinyl chloride, or any other material suitable for extrusion. In particular, it is preferred to use polyolefin based TPE materials, such as Mediprene OF 600M and OF900M, or TPU, such as Tecoflex EG 100A and EG 80 A. The above-discussed materials are in particular well suited for production by means of extrusion. However, other materials, such as e.g. latex and/or silicone, may also be used, especially if other production methods, such as injection molding or dipping, are considered.

The materials used for the two or more zones may be entirely different materials or blends, or may be various grades of the same material or blend. The two materials may also be essentially the same material, but made different by means of added plasticizers, softeners, fillers, medical oil (i.e. oil of a medical grade), paraffin, etc. The materials can also be provided with different properties by treatment of the materials in different ways In order to obtain good properties for handling, painless and easy insertion, etc, the materials of the tubular shaft are preferably prepared and composed in such a way that they fulfill at least some of the following requirements, and preferably essentially all of them:

It is preferred that the materials are capable of being sterilized by known sterilization methods. In particular it is preferred that the materials have a radiation resistance such that it can endure at least 50 kGy essentially without degradation, in order to enable radiation sterilization of the urinary catheter.

The materials should preferably have good kinking properties.

The materials should preferably be biocompatible.

The materials should preferably be meltprocessable, extrudable, or usable for molding, in particular injection molding.

The materials should preferably have good dimension stability. In particular, it is preferred that the longitudinal shrinkage of the catheters as a result of the coating process is less than 5%, and preferably less than 1%, of the original length.

The tubular shaft is preferably at least partly coated with a hydrophilic surface coating, the coating preferably covering at least an insertable part of the catheter, said hydrophilic surface coating exhibiting a low friction when wetted.

The hydrophilic polymer may be at least one of: polyvinyl compounds, polylactames, in particular such as polyvinyl pyrrolidones, polysaccharides, in particular heparin, dextran, xanthan gum, derivatised polysaccharides, hydroxy propyl cellulose, methyl cellulose, polyurethanes, polyacrylates, polyhydroxyacrylates, polymethacrylates, polyacrylamides, polyalkylene oxides, in particular polyethylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anyhydride, polyactide, polyethylene glycol and copolymers thereof. Preferably, the hydrophilic polymer is polyvinyl pyrrolidone.

The hydrophilic coating preferably forms a polyurea network, and most preferably the polyurea network is arranged to form a covalent bond to active hydrogen groups in the substrate. Alternatively, the hydrophilic coating may form an ester bond or an epoxy bond to active hydrogen groups in the substrate.

According to one embodiment, coating of the substrate material of the catheter may be made by a process comprising the steps of: applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature.

However, other hydrophilic coatings are also feasible, such as a coating comprising hydrophilic polymers cross-linked directly to the substrate. The cross-linking may be effected by means of irradiation, e.g. by electron beams or UV light.

In case the two or more materials used in the two or more zones of the tubular shaft are different in respect of coatability, i.e. how well the intended coating adheres and functions, the material having best coatability is preferably as far as possible arranged on the exterior surface of the tubular shaft, at least in the insertable part of the tubular shaft.

The catheter is preferably arranged in a package, to maintain it sterile prior to use.

The catheter preferably has a radiation resistance such that it can endure at least 50 kGy essentially without degradation. Hereby, radiation sterilization of the medical device can be used, without affecting the properties of the medical device.

According to another aspect of the present invention, there is provided a method for producing a urinary catheter, comprising forming of a tubular shaft, and arrange an insertion end a discharge end at ends thereof, the tubular shaft being formed of at least two materials having different properties, each of said materials being arranged substantially separated from each other in distinct zones, at least one of said distinct zones preferably extending over essentially the entire length of the tubular shaft, wherein at least one of the width and thickness of said zones varies over the length of the tubular shaft, to form two or more uniform sections of the tubular shaft having various relative amounts of said materials, and wherein at least one transition between two of said uniform sections is formed by at least one transition section providing a gradual transition between said uniform sections.

Hereby, similar advantages and properties are obtained as discussed above in relation to the first aspect of the invention.

The tubular shaft is preferably made by intermittent extrusion. "Intermittent extrusion" here refers to an extrusion process in which two or more materials are extruded, at least to some extent simultaneously, and where the flow rate of the two or more materials varies over time. Since at least one of the materials is provided continuously, but in varying flow rate, the extrusion process becomes very efficient, and with increased controllability. This manufacturing is very beneficial, since the extruded tubes are very cost-effective to produce, and also have very good properties, such as a very well-defined and even wall thickness.

In one embodiment two or more tubular shafts are formed simultaneously, through two separate extrusion nozzles, the formation of said tubular shafts being offset in relation to each other. In this way, the total flow rate of the two materials can be controlled to be even more uniform, or even more or less constant, whereas the flow rate of the two or more materials into the individual extrusion nozzles is allowed to vary significantly. Preferably, the offset between the two or more tubular shafts is set so that an essentially constant flow rate of said two or more materials are expelled through said extrusion nozzles (in combination).

However, other production methods apart from extrusion are also feasible, such as production by two (or more) component injection molding.

These and other aspects of the invention will be apparent from and elucidated with reference to the embodiment described hereinafter.

BRIEF DESCRIPTION OF THE DRAWINGS

By way of example embodiments of the invention will now be described with reference to the accompanying drawings in which.

DESCRIPTION OF PREFERRED EMBODIMENTS

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

The following discussion is in particular concerned with hydrophilic urinary catheters for intermittent use. However, the invention can also be used in relation to other types of urinary catheters, such as for indwelling urinary catheters and for non-hydrophilic intermittent catheters.

Figure 1:
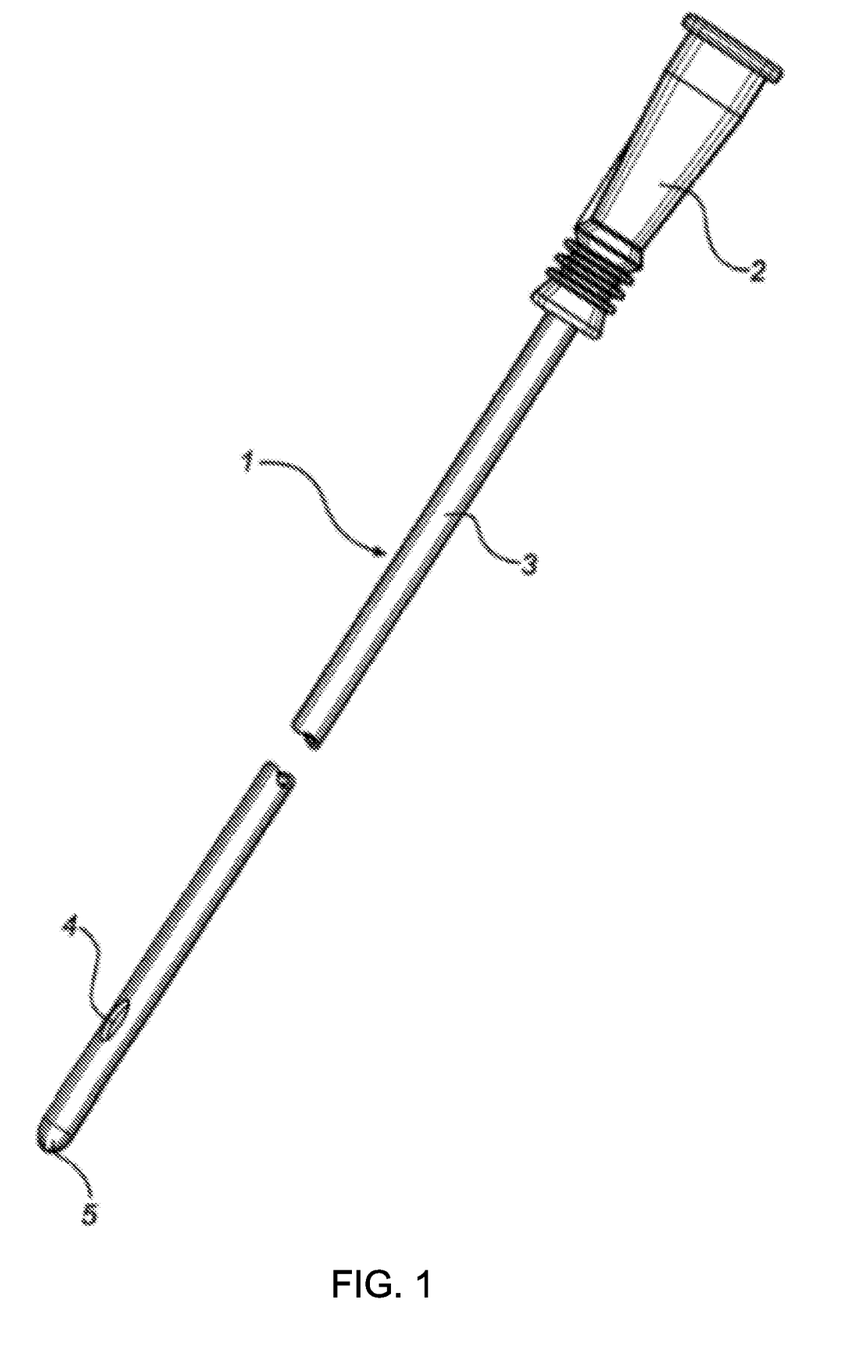
FIG. 1 illustrates an embodiment of a catheter according to the invention.

A general urinary catheter 1 of the type to which the present invention pertains is illustrated in FIG. 1, and comprises a flared rearward portion 2 at the discharge end and an elongate tubular 3 projecting forwardly from the rearward portion 2. An open-ended internal lumen (not shown) extends from the discharge end (the rear end) of the rearward portion 2 to a drainage aperture 4 in a rounded tip 5, the insertion tip, of the tubular shaft 3. The catheter preferably has only one, single internal lumen. The one or more drainage openings are preferably arranged close to the insertion end of the catheter. The insertable tip of the catheter is preferably closed, and is preferably formed in a rounded shape. The rearward portion 2 is preferably formed as a flared end, and may function as a connector of the catheter 1, being connectable to other devices, such as a urine collection bag, a drainage tube or the like.

At least a part of the elongate tubular shaft 3 forms an insertable length to be inserted through a body opening of the user, such as the urethra in case of a urinary catheter. By insertable length is normally meant that length of the tubular shaft 2 which is insertable into the urethra of the patient. Typically, this will be 80-140 mm for a female patient and 200-350 mm for a male patient. At least the insertable part of the catheter is preferably provided with a hydrophilic surface layer, to be discussed in more detail in the following.

The catheter is preferably arranged in a closed receptacle, functioning as a package, and optionally also as a sterile barrier, in a sterilized state. The receptacle houses at least the insertable part of the catheter, and possibly the entire catheter, and preferably also a wetting fluid to maintain the catheter in an activated, wetted state, in case the catheter is a hydrophilic catheter. Hereby, the catheter becomes immediately ready to use upon withdrawal from the package. Alternatively, the wetting fluid may be arranged in a separate compartment or container connected to or arranged within the receptacle, and to be released for wetting of the catheter prior to use. Further, the wetting fluid need not be present in liquid form, but may also be present in the form of gas, e.g. by providing a moist, vapor containing atmosphere in the container. However, the catheter may also be stored in a dry state. In such a case, the wetting fluid may be arranged in a separate compartment or pouch of the package, for wetting and activation of the catheter immediately prior to use. When maintained in a dry state, it is also possible to wet the catheter with a wetting fluid provided from an external supply. The catheter may also be a non-hydrophilic coating or the like, where no additional wetting fluid is needed for activation of the catheter surface. The wetting fluid is preferably a water-based liquid, i.e. using plain water or a solution comprising water as a solvent, such as saline or other.

Reference is now made to FIGS. 2-9, showing different embodiments of the structure of the tubular shaft. The tubular shaft is formed of at least two materials having different properties and the materials are arranged substantially separated from each other in distinct zones, ZS and ZH. The materials have different properties, and in particular it is preferred that the materials have different stiffness, so that the material forming zone ZS is relatively softer and more flexible than the material forming zone ZH, which is then relatively stiffer and more rigid. The materials thus preferably differ in hardness, bending stiffness, tensile modulus, flexibility and/or elasticity. Preferably, the materials also differ in color, or are otherwise visibly discernible from each other, such as having various degrees of opaqueness/transparency.

At least one of these distinct zones extends over essentially the entire length of the tubular shaft. Further, the width and/or the thickness of the zones varies over the length of the tubular shaft, to form two or more uniform sections S, H of the tubular shaft having various relative amounts of these different materials. Further, at least one transition between two such uniform sections is formed by at least one transition section T providing a gradual transition between the uniform sections. In the transition sections T, there is a gradual transition between the width or thicknesses of the zones between said different uniform sections.

Figure 2:
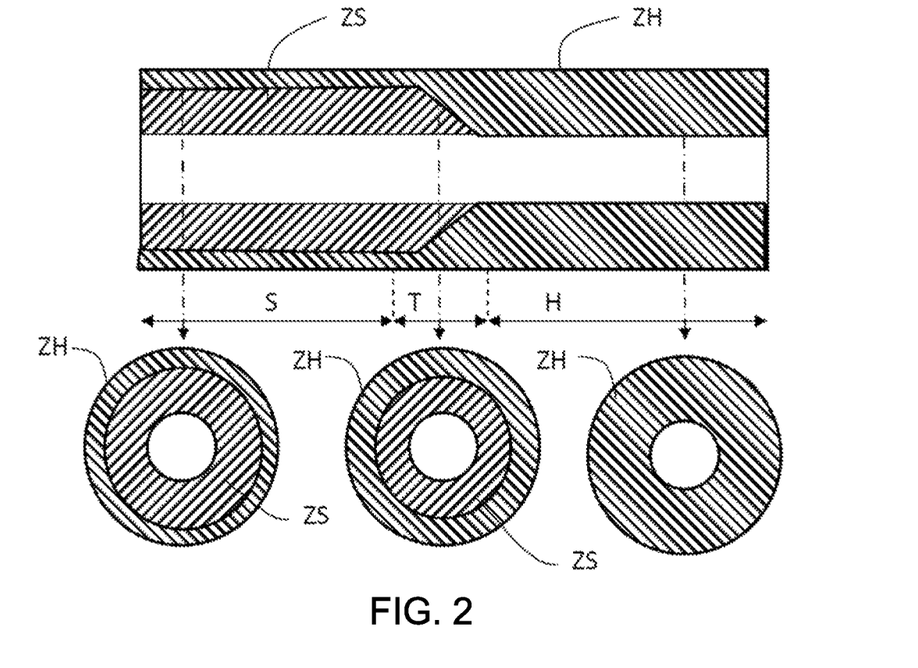
FIG. 2 shows cross-sectional views in a length direction and in several radial directions of a tubular shaft in accordance with an embodiment of the catheter of the invention.

In one embodiment, illustrated in FIG. 2, the zones ZS and ZH are arranged as layers, extending around the circumference of the tubular shaft. In this embodiment, one of the zones, ZH, being of the relatively stiffer material, extends over the entire length of the tubular shaft. This layer is arranged outwardly, and forms the exterior surface of the tubular shaft. In one uniform section S, the zone ZH is relatively thin, and the underlying layer of the relatively soft material, ZS, is relatively thick. In another uniform section H, the tubular shaft is formed entirely of the relatively rigid material, ZH. In an intermediate transition section, T, there is a gradual transition of the thicknesses of the different material layers. Hereby, the tubular shaft is provided with an exterior surface formed by the same material over the entire outer surface, but being provided with a softer section at one end, a stiffer section at another end, and a gradual transition between these sections.

Figure 3:
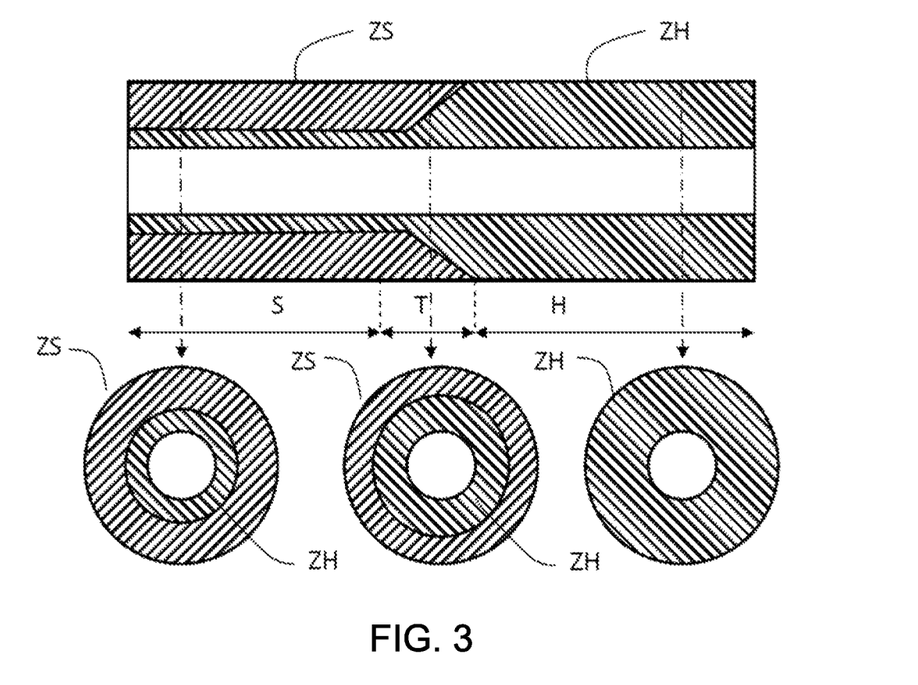
FIG. 3 shows cross-sectional views in a length direction and in several radial directions of a tubular shaft in accordance with another embodiment of the catheter of the invention.

In another embodiment, illustrated in FIG. 3, the zones ZS and ZH are again arranged as layers, extending around the circumference of the tubular shaft. In this embodiment, one of the zones, ZH, being of the relatively stiffer material, extends over the entire length of the tubular shaft. This layer is arranged inwardly, and forms the interior surface of the tubular shaft. In one uniform section H, the section is formed entirely of the stiffer material ZH. In another section, S, there is provided one relatively thin layer of the stiffer material, ZH, and one relatively thick layer of the softer material, ZS. In an intermediate transition section, T, there is a gradual transition of the thicknesses of the different material layers. Hereby, the tubular shaft is provided with an interior surface formed by the same material over the entire outer surface, but being provided with a softer section at one end, a stiffer section at another end, and a gradual transition between these sections.

Figure 4:
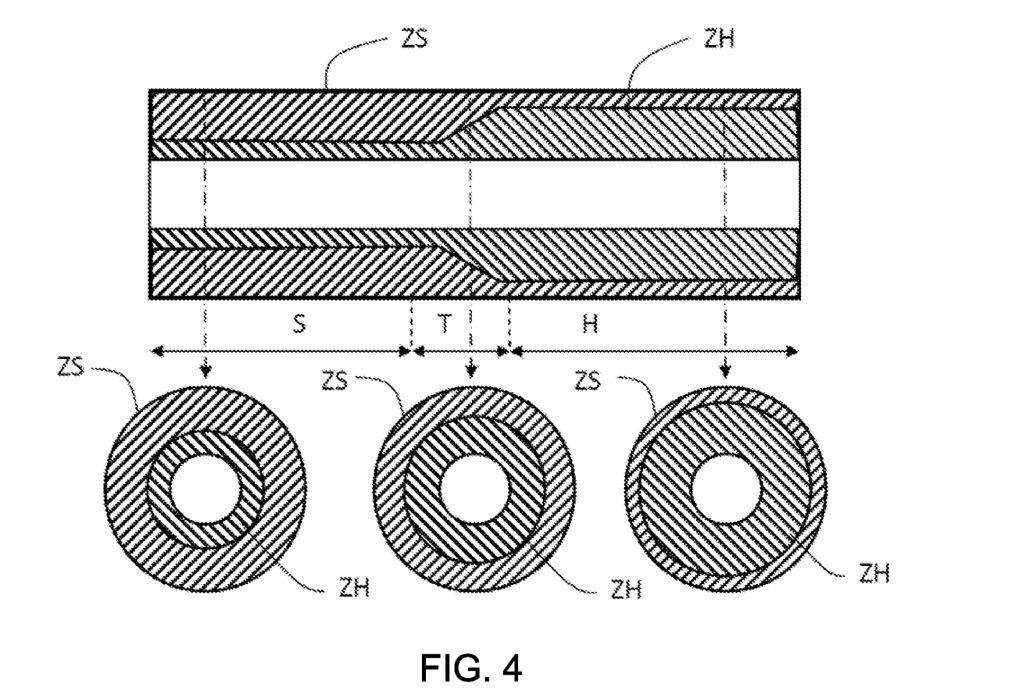
FIG. 4 shows cross-sectional views in a length direction and in several radial directions of a tubular shaft in accordance with another embodiment of the catheter of the invention.

In another embodiment, illustrated in FIG. 4, the zones ZS and ZH are again arranged as layers, extending around the circumference of the tubular shaft, and both extending continuously over the length of the tubular shaft. In this embodiment, both of the zones, ZS, ZH being of the relatively softer and stiffer material, respectively, extend over the entire length of the tubular shaft. These layers are arranged inwardly and outwardly, and form the interior and exterior surfaces of the tubular shaft. In one uniform section S, the section is formed of a relatively thick layer of the softer material, ZS, and a relatively thin layer of the stiffer material, ZH. In another section, H, the section is formed of a relatively thick layer of the stiffer material, ZH, and a relatively thin layer of the softer material, ZS. In an intermediate transition section, T, there is a gradual transition of the thicknesses of the different material layers. Hereby, the tubular shaft is provided with both an interior and exterior surface formed by the same materials over the entire outer and interior surfaces, but being provided with a softer section at one end, a stiffer section at another end, and a gradual transition between these sections.

Figure 5:
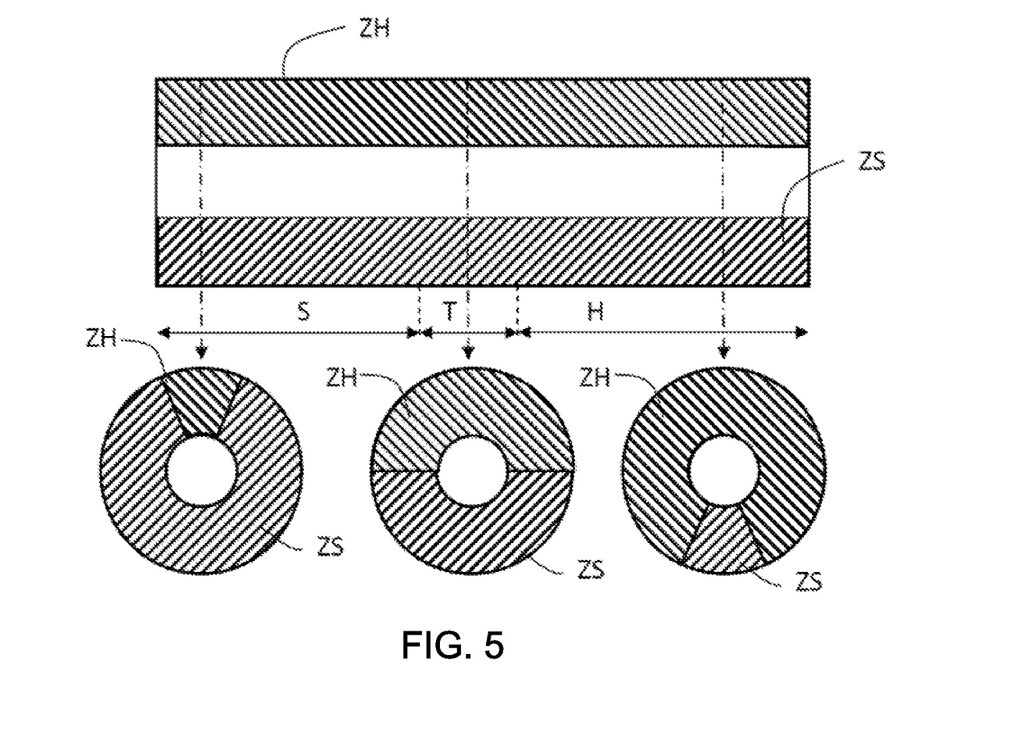
FIG. 5 shows cross-sectional views in a length direction and in several radial directions of a tubular shaft in accordance with another embodiment of the catheter of the invention.

In another embodiment, illustrated in FIG. 5, the zones ZS and ZH are arranged as strips, extending along the length of the tubular shaft, and having varying widths. In one uniform section S, the section is formed of a relatively widely extending strip of the softer material, ZS, and a relatively narrow strip of the stiffer material, ZH. Both strips here extend over the entire thickness of the tubular shaft. In another section, H, the section is formed of a relatively wide strip of the stiffer material, ZH, and a relatively narrow strip of the softer material, ZS. In an intermediate transition section, T, there is a gradual transition of the widths of the different material strips. Hereby, the tubular shaft is provided with an asymmetric distribution of the softer and stiffer materials, and a gradual transition between these sections.

Figure 6:
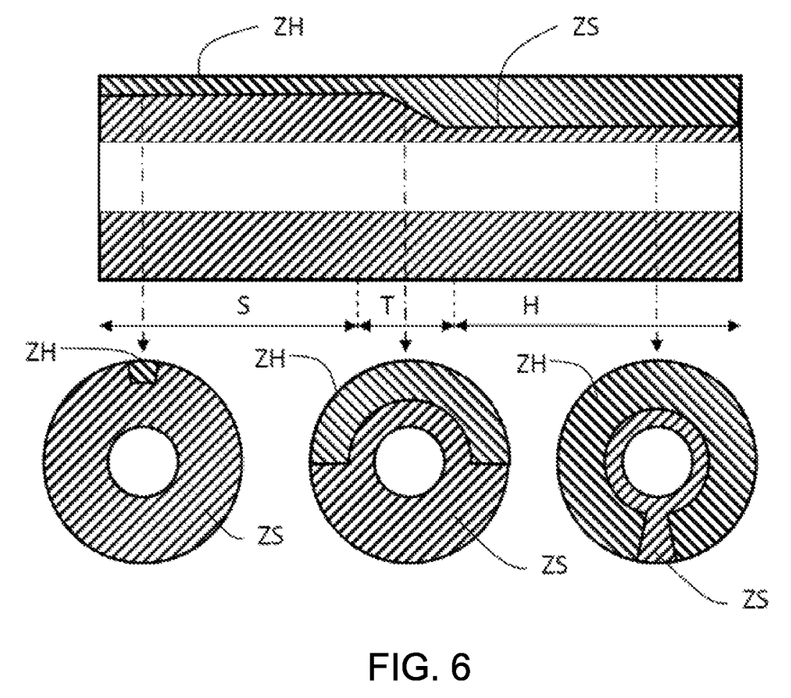
FIG. 6 shows cross-sectional views in a length direction and in several radial directions of a tubular shaft in accordance with another embodiment of the catheter of the invention.

In another embodiment, illustrated in FIG. 6, the zones ZS and ZH are again arranged as strips, extending along the length of the tubular shaft, and having varying widths. In one uniform section S, the section is formed of a relatively widely extending strip of the softer material, ZS, and a relatively narrow strip of the stiffer material, ZH. Here, however, the strip of the stiffer material, ZH, only extends over a limited part of the thickness of the tubular shaft, and being arranged towards the exterior surface. In another section, H, the section is formed of a relatively wide strip of the stiffer material, ZH, again arranged towards the exterior surface, and a relatively narrow strip of the softer material, ZS. Again, the thickness of the harder material, ZH, is limited. In an intermediate transition section, T, there is a gradual transition of the widths of the different material strips. Hereby, the tubular shaft is provided with an asymmetric distribution of the softer and stiffer materials, and a gradual transition between these sections. In this embodiment, the interior surface of the tubular shaft is entirely formed by the softer material, ZS.

Figure 7:
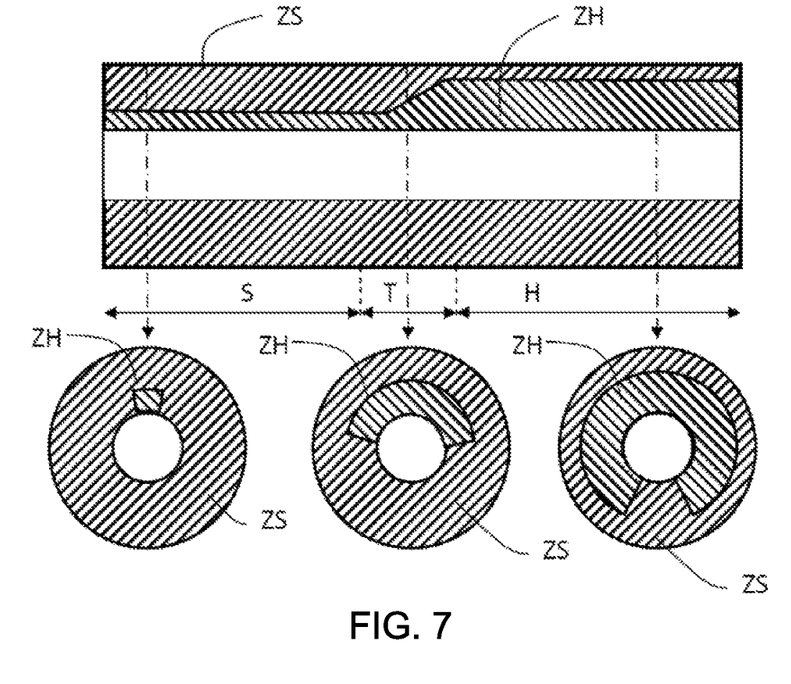
FIG. 7 shows cross-sectional views in a length direction and in several radial directions of a tubular shaft in accordance with another embodiment of the catheter of the invention.

In another embodiment, illustrated in FIG. 7, the zones ZS and ZH are again arranged as strips, extending along the length of the tubular shaft, and having varying widths. In one uniform section S, the section is formed of a relatively widely extending strip of the softer material, ZS, and a relatively narrow strip of the stiffer material, ZH. Here, however, the strip of the stiffer material, ZH, only extends over a limited part of the thickness of the tubular shaft, and being arranged towards the interior surface. In another section, H, the section is formed of a relatively wide strip of the stiffer material, ZH, again arranged towards the interior surface, and a relatively narrow strip of the softer material, ZS. Again, the thickness of the harder material, ZH, is limited. In an intermediate transition section, T, there is a gradual transition of the widths of the different material strips. Hereby, the tubular shaft is provided with an asymmetric distribution of the softer and stiffer materials, and a gradual transition between these sections. In this embodiment, the exterior surface of the tubular shaft is entirely formed by the softer material, ZS.

Figure 8:
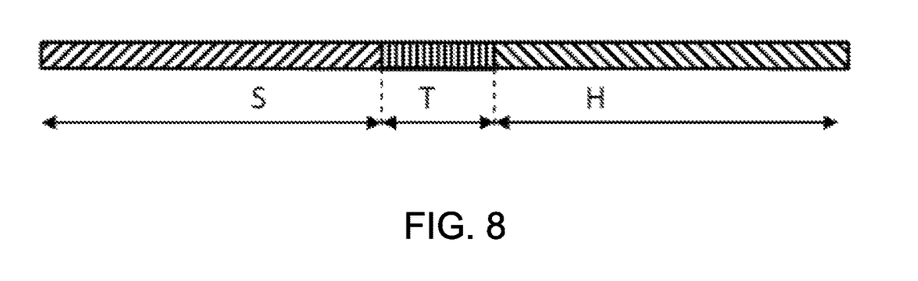
FIG. 8 is a schematic illustration of the arrangement of different sections in a tubular shaft of a catheter in accordance with an embodiment of the invention.

In one embodiment, illustrated in FIG. 8, the tubular shaft comprises a uniform section S being closest to the insertion end which is softer than another section H being farther away from the insertion end. In this embodiment, the shaft only comprises these two uniform sections, and with a transition section T there between. Each of the two sections preferably extends over at least 25% of the total length of the catheter shaft, and preferably over at least 40%, and most preferably over at least 45%. Thus, for a male catheter, typically having a catheter shaft being 30-40 cm long in total, the softer forward section S may be 8-19 cm long, and preferably 12-18 cm, and the stiffer rearward section H may have a similar length.

However, more than one softer uniform section and/or more than one stiffer uniform section may also be provided, and distributed in the longitudinal direction.

Figure 9:
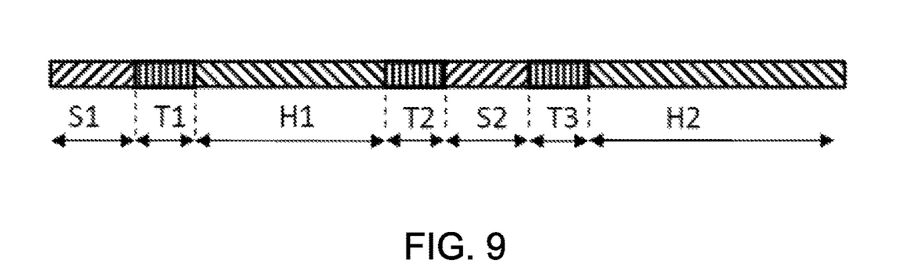
FIG. 9 is a schematic illustration of the arrangement of different sections in a tubular shaft of a catheter in accordance with another embodiment of the invention.

In another embodiment, illustrated in FIG. 9, the tubular shaft comprises four uniform sections, at least two being relatively softer and at least two being relatively stiffer, the softer and stiffer sections being arranged in an alternating fashion along the length of the catheter shaft, and with transition sections being arranged between all adjacent uniform sections. Thus, in this embodiment, there is a first softer uniform section S1 arranged closest to the insertion end, a first transition section T1, followed by a first stiffer uniform section H1, a second transition section T2, a second softer uniform section S2, a third transition section T3, and a second stiffer uniform section H2. The stiffer uniform sections H1 and H2 are preferably longer than the softer uniform sections S1 and S2, and also preferably longer than the transition sections T1-T3. Preferably, the stiffer uniform sections are at least twice as long. Hereby, the tubular shaft is overall relatively stiff, but with certain parts being made softer. For example, the softer parts at or close to the insertion aid, i.e. sections S1 and to some extent T1, facilitates insertion of the catheter, since the soft tip enables the catheter to navigate and find its way into the curved urethra. Further, the second softer section S2, and to some extent the transition sections T2 and T3, provides softness and flexibility to the middle of the catheter and/or the middle of the insertable part of the tubular shaft. Hereby, the catheter is gentler to the urethra during use, and in particular to the suspensory ligament and/or the membranous part of the urethra. Hereby, catheterization is made more comfortable and with reduced risk of harming or damaging the urethra. This softer section in the middle also facilitates storing of the catheter in a folded disposition.

Figure 10:
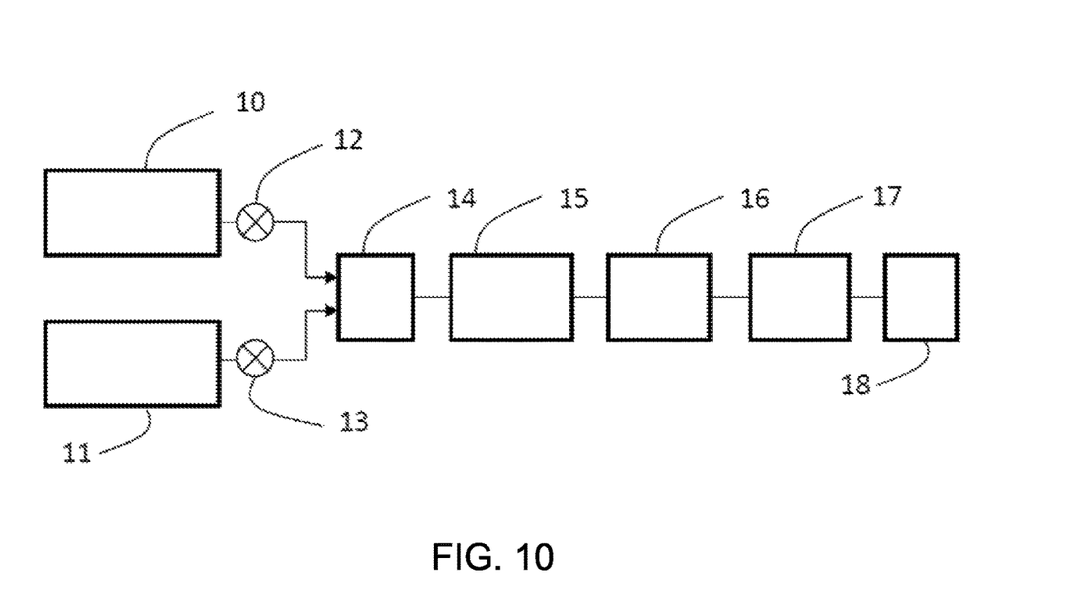
FIG. 10 is a schematic overview of an extrusion system for producing catheters in accordance with the invention.

The tubular shaft is preferably produced by intermittent extrusion. An extrusion system for use in such production is schematically illustrated in FIG. 10. The system comprises two extruders 10, 11, each arranged to provide one of the two materials. In case more than two materials, more extruders may be added to the system. The material from the extruders are fed to an extrusion head or extrusion nozzle arrangement 14, in which the materials are co-extruded in a desired fashion, as discussed above. The flow rates of the two materials are controller by modulating members 12, 13, such as valves or the like. A controller (not shown) is preferably provided and arranged to continuously controlling the extruders, the modulating members and the extrusion nozzle arrangement, in order to obtain the desired formation of zones in the produced tube.

After discharge from the extrusion nozzle arrangement 14, the extruded tube may be cooled in a cooling arrangement or cooler, such as a water bath 15. The system may further be provided with a drying arrangement or dryer 16, a pulling arrangement or puller 17 and a cutting arrangement or cutter 18, to cut the extruded tube into tubular shafts of the desired length, etc. However, alternatively, the extruded tube may be taken-up by a winding device or the like. Also, as is per se known in the art of extrusion, any or all of these parts following the extrusion nozzle may be omitted, replaced with other, similar arrangements, be complemented with additional parts, etc.

The provision of one or both of the materials continuously during the extrusion is highly advantageous, since the extrusion system can hereby operate more efficiently, and be more precisely controlled.

Figure 11:
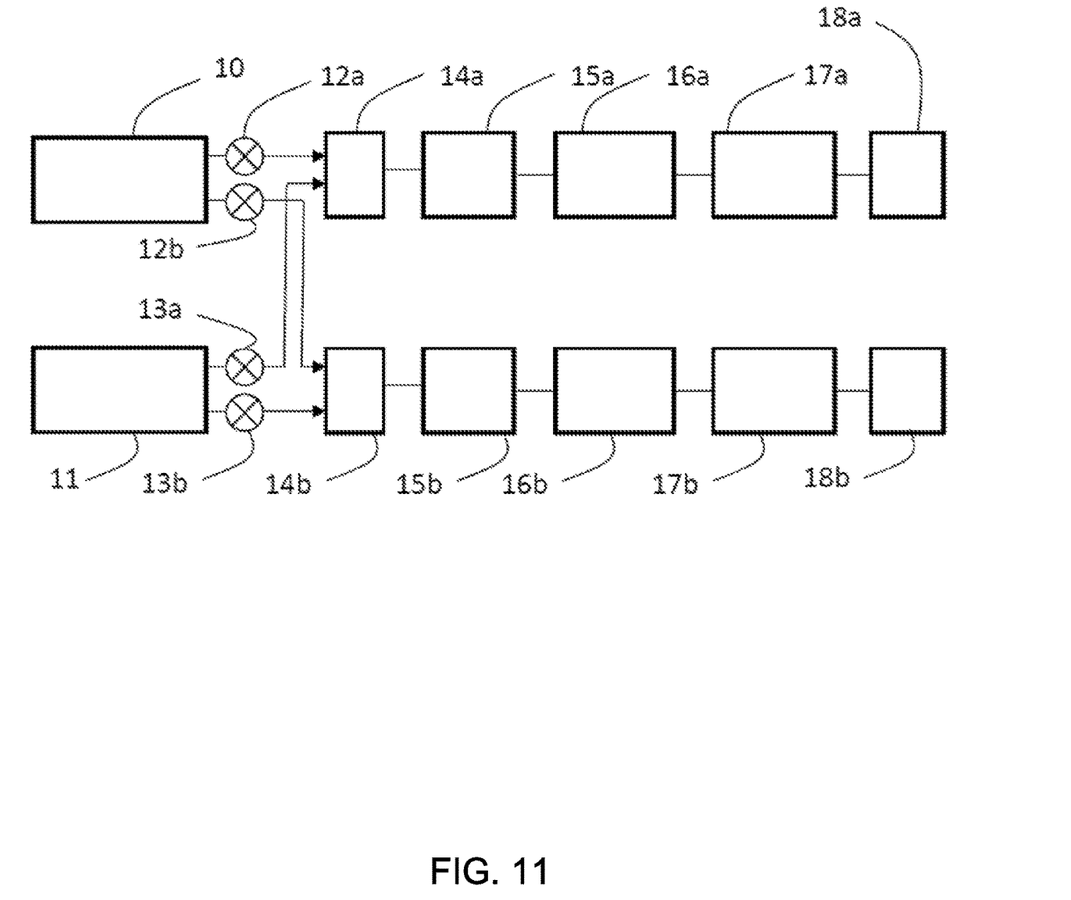
FIG. 11 is a schematic overview of another embodiment of an extrusion system for producing catheter in accordance with the invention.

It is also possible to manufacture two or more tubes simultaneously. Hereby, the materials provided by the extruders can be provided to two or more extrusion nozzle arrangements. Such an embodiment is illustrated in FIG. 11, in which the material from extruder 10 is controlled by modulation members 12*a*, 12*b* to be provided to extrusion nozzle arrangements 14*a* and 14*b*, and in the same way the material from extruder 11 is controlled by modulation members 13*a*, 13*b* to be provided to the same extrusion nozzle arrangements 14*a*, 14*b*. The system may be controlled to produce tubular shafts in the extrusion nozzle arrangements 14a, 14b in such a way that the tubular shafts are produced differently in the two extrusion nozzle arrangements. For example, one extrusion nozzle arrangement may produce tubular shafts with the insertion end first, whereas the other extrusion nozzle arrangement may produce tubular shafts with the rearward end first. For tubular shafts as discussed e.g. in relation to FIG. 8 above, this means that an essentially constant flow of both materials may be provided by the extruders 10, 11, whereas the flow rate of the two materials into the two extrusion nozzle arrangements varies over time. Alternatively, it is also possible to offset the production of the tubular shafts in the two extrusion nozzle arrangements, so that the production is controlled at least to some extent in such a way that when a stiffer section H is produced by one of the extrusion nozzle arrangements, a softer section is produced by the other extrusion nozzle arrangement, and vice versa. This also provides a more uniform flow rate of materials out from the extruders, which in a similar way makes the extrusion process more efficient and more precisely controllable. After the extrusion nozzles, further devices or parts 15a-18a, 15b-18b may be provided, as discussed in the previous example, and may be provided in two separate lines, as shown in FIG. 8, or in a common line (not shown).

Extrusion nozzles for extrusion of two or more materials simultaneously is per se previously known, and described e.g. in U.S. Pat. Nos. 5,533,985, 4,250,072, 5,258,160 and US 2008/0193583, all of said documents hereby being incorporated in their entirety by reference. The extrusion nozzle, or extrusion die, preferably has two outlet openings, i.e. forming a bi-orifice tubular extrusion die.

After production of the tubular shaft, the rearward end and tip may be formed in any desired way.

For example, the rearward part may be formed as a flared rearward part by insertion of at least one conical mandrel into the tube end during application of heat. Thus, a relative movement between the tubular shaft and the mandrel pushes the end of the tubular shaft onto the conical mandrel, thereby expanding and flaring the end of the tubular shaft into the shape of the mandrel. However, it is also possible to connect a separately produced connector to the tubular shaft by gluing or the like, as is per se well known in the art. Such a separately produced connector may e.g. be produced by injection molding, and can be connected to the end of the tubular shaft by gluing, welding or the like.

Further, the tip portion at the end of the tubular shaft being opposite the rearward end may be formed into a desired shape by means of e.g. melting. Further, at least one, and preferably two or more, drainage openings in the side wall of the tubular shaft can be provided. This may be accomplished by punching, with punching means, or blank cutting. However, it is also feasible to connect a separately produced tip to the end of the tubular shaft, e.g. by gluing, as is per se known in the art. Such a separately produced tip can e.g. be produced by injection molding, and be connected to the end of the tubular shaft by gluing, welding or the like.

The tip may be straight, extending in the same direction as the tubular shaft and forming a rounded forward end. This tip type is generally known as a Nelaton type catheter. In such an embodiment, the tip preferably has an outer diameter which at all places is equal to or lower than the outer diameter of the tubular shaft. The tip is preferably arranged conically tapering in the forward direction, to end in a rounded tip. Alternatively, the tip may be enlarged, thereby presenting at least a part having a larger outer diameter than the catheter shaft. For example, enlarged tip may be in the form of a bulb or the like.

The drainage openings are preferably provided as openings, so-called catheter eyes, in the sidewall of the tip and/or in the forward end of the tubular shaft. However, it is also possible to use, additionally or as an alternative, a drainage opening being centrally arranged along the longitudinal axis of the catheter. Here, the forward end of the catheter and tip are not closed, and the drainage opening is formed in the extension of the internal lumen of the catheter.

Also, the tip may be curved, forming a Tiemann or Coude type catheter.

The catheters may be made in various lengths and dimensions. Typically, the length of the catheter tube for female catheters are in the range 50-200 mm, such as with a length in the size of about 8, 10 or 12 cm, preferably corresponding to a total catheter length of about 11, 13 or 15 cm, and for male catheters may preferably in a length in the range of 180-450 mm, such as in the size of about 32, 34 or 36 cm, preferably corresponding to a total catheter length of about 36, 38 or 40 cm, respectively. The indicated total catheter lengths here refer to the length of the catheter tube and the flared end/connector together. The outer diameter of the tube after drying/cooling is preferably constant, and in the range 2-7 mm, and more preferably in the range 4-6 mm. The inner diameter of the tube after drying/cooling is preferably constant, and in the range 1.4-5 mm, and more preferably in the range 2.6-4 mm. The thickness of the tube after drying/cooling is preferably constant, and in the range 0.5-4 mm, and more preferably in the range 1-3 mm, and most preferably in the range 1.5-2 mm.

EXAMPLES

In a first example, tubular shafts were produced by means of intermittent extrusion, as discussed above, and structure in the way discussed above in relation to FIG. 8, with a softer section, an intermediate transition section, and a stiffer section. Both materials were provided continuously over the entire length of the tubular shaft, in the way discussed above in relation to FIG. 5, and with a diagonal transition in the transition section.

In this first example, the tubular shaft was made by two polyolefin based TPE blend materials, commercially available as Mediprene OF 900M and OF 600M.

The tubular shafts were formed into catheters, and coated with a hydrophilic coating by applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature.

The produced catheters were evaluated, and also, as a reference, compared to LoFric® catheters, commercially available from Wellspect Healthcare.

The catheters were produced in the sizes Ch 12, 14 and 16; corresponding to an outer diameter of the tube of 4, 4.66 and 5.33 mm.

First, the hardness of the soft and stiff segments of the catheters where measured with a micro Shore A method, and the result is presented in the following table 1.

TABLE 1

Hardness

| Catheter size/segment | μShoreA |
|---|---|
| Ch 12 soft | 55 |
| Ch 12 stiff | 73 |
| Ch 14 soft | 55 |
| Ch 14 stiff | 80 |
| Ch 16 soft | 53 |
| Ch 16 stiff | 86 |

As can be seen from the table, there is a significant difference between the softer and stiffer sections, where the softer sections have a μshore A hardness in the range 50-60, and the stiffer sections in the range 70-90. Most commercially available hydrophilic urinary catheters have a hardness of about 75-80, and notably the softer section here has a significantly lower hardness, whereas the stiffer section has a similar, or even somewhat higher hardness than in conventional urinary catheter.

Further, bending stiffness was measured, both on raw catheters and catheters that were coated. From this, a tensile modulus was also calculated. In order to calculate the tensile modulus, the inner and outer diameters of the catheters were measured. The Ch 12 catheters had inner diameters in the range 2.1-2.5 mm, and outer diameters in the range 3.6-4.2 mm. The Ch 14 catheters had inner diameters in the range 2.9-3.1 mm, and outer diameters in the range 3.8-4.8 mm. The Ch 16 catheters had inner diameters in the range 3.1-3.3 mm, and outer diameters in the range 5.1-5.4 mm. As a reference, a LoFric® catheter was measured as well. This catheter was a Ch 12 catheter, having an inner diameter of 2.6 mm, and an outer diameter of 4.0 mm. The result is presented in the following Table 2.

TABLE 2

Bending stiffness and tensile modulus

| Catheter | Bending stiffness (MPa * mm$^4$) | Tensile modulus (MPa) |
|---|---|---|
| Ch 12, soft, raw | 35 | 3.8 |
| Ch 12, stiff, raw | 187 | 18.9 |
| Ch 14, soft, raw | 75 | 3.5 |
| Ch 14, stiff, raw | 425 | 18.3 |
| Ch 16, soft, raw | 113 | 3.4 |
| Ch 16, stiff, raw | 684 | 20.3 |
| Ch 12, soft, coated | 32 | 4.4 |
| Ch 12, stiff, coated | 251 | 24.6 |
| Ch 14, soft, coated | 77 | 3.7 |
| Ch 14, stiff, coated | 460 | 20.6 |
| Ch 16, soft, coated | 129 | 3.8 |
| Ch 16, stiff, coated | 640 | 21.4 |
| Ch 12, LoFric | 178 | 17.4 |

It can be noted that the bending stiffness for the softer sections is in the range 25-150 MPa*mm$^4$, which is lower or much lower than for the conventional reference catheter (Ch 12, LoFric). The stiffer sections have a bending stiffness in the range 160-720 MPa*mm$^4$, which covers the bending stiffness for the reference catheter, but is generally much higher.

The tensile modulus for the softer sections is in the range 3-6 MPa, which is much lower than for the conventional reference catheter, whereas the tensile modulus for the stiffer sections, being in the range 15-30 MPa, covers the tensile modulus of the reference catheter, but is generally much higher.

The coated catheters were also manually evaluated, in order to determine slipperiness and roughness. The catheters were graded from 1-10, where 10 corresponds to zero friction and a completely smooth surface, respectively. Values above 8 are considered extremely good, corresponding to the best catheters presently available on the market. Again, a comparison was made with the same reference catheter. The result is presented in the following table 3.

TABLE 3

Result from manual evaluation of the catheters

| Catheter | Slipperiness | Roughness |
|---|---|---|
| Softer section | 9 | 9 |
| Stiffer section | 9 | 9 |
| Reference (LoFric Ch 12) | 9 | 8 |

Thus, it can be seen that the coating of the examples is very good, and performs as well, and even slightly better, than the reference catheter.

The friction of the coated catheters was finally determined with a Harland FTS Friction tester, available from Harland Medical Systems, with a clamp force of 100 g and a pull speed of 1.0 cm/s. Again a comparison was made with the LoFric reference. It was determined that the friction coefficient for the stiffer sections was extremely good (about 0.008), even lower than for the LoFric reference (which had a friction coefficient of about 0.021). The softer sections material had a slightly higher, but still fully acceptable friction coefficient of about 0.025.

In a second example, the catheters were produced and structured in the same way as in the first example, but made of different materials. In this second example, the tubular shafts were made by TPU material, and more specifically Tecoflex EG 80A and Tecoflex EG 100A, both commercially available from Lubrizol.

Again, the hardness of the soft and stiff segments of the catheters where measured with a micro Shore A method, and the result is presented in the following table 4.

TABLE 4

Hardness

| Catheter size/segment | μShoreA |
|---|---|
| Ch 12 soft | 65 |
| Ch 12 stiff | 89 |
| Ch 14 soft | 65 |
| Ch 14 stiff | 91 |
| Ch 16 soft | 67 |
| Ch 16 stiff | 93 |

As can be seen from the table, there is also in this example a significant difference between the softer and stiffer sections, where the softer sections have μShoreA hardness in the range 63-68, and the stiffer sections in the range 85-94. Most commercially available hydrophilic urinary catheters have a hardness of about 75-80, and notably the softer section also here has a significantly lower hardness, whereas the stiffer section has a similar, or even somewhat higher hardness than in conventional urinary catheters.

Further, bending stiffness was measured, in the same way as discussed above in relation to the first example. The result is presented in the following Table 5.

TABLE 5

Bending stiffness and tensile modulus

| Catheter | Bending stiffness (MPa * mm$^4$) | Tensile modulus (MPa) |
|---|---|---|
| Ch 12, soft, raw | 30 | 4.0 |
| Ch 12, stiff, raw | 479 | 40.3 |
| Ch 14, soft, raw | 55 | 3.2 |
| Ch 14, stiff, raw | 632 | 38.9 |
| Ch 16, soft, raw | 119 | 2.7 |
| Ch 16, stiff, raw | 1530 | 42.2 |
| Ch 12, soft, coated | 33 | 4.4 |
| Ch 12, stiff, coated | 382 | 37.1 |
| Ch 14, soft, coated | 31 | 2.3 |
| Ch 14, stiff, coated | 631 | 34.3 |
| Ch 16, soft, coated | 31 | 1.0 |
| Ch 16, stiff, coated | 1430 | 42.4 |

It can be noted that the bending stiffness for the softer sections is in the range 15-140 MPa*mm$^4$, which is lower or much lower than for the conventional reference catheter (Ch 12, LoFric—see above). The stiffer sections have a bending stiffness in the range 120-2000 MPa*mm$^4$, which covers the bending stiffness for the reference catheter, but is generally much higher.

The tensile modulus for the softer sections is in the range 0.5-5 MPa, which is much lower than for the conventional reference catheter, whereas the tensile modulus for the stiffer sections, being in the range 20-65 MPa, covers the tensile modulus of the reference catheter, but is generally much higher.

Further, the coating of the coated catheters was evaluated, in the same way as for the first example and were all found fully acceptable.

CONCLUDING REMARKS

The person skilled in the art realizes that the present invention by no means is limited to the preferred embodiments described above. On the contrary, many modifications and variations are possible within the scope of the appended claims. For instance, the urinary catheter need not have a flared rearward part, but may instead end with the end of the tubular shaft, and also need not have a rounded, closed tip, but may instead end with the tubular shaft itself. Further, in case a closed tip is used, the tip may be either straight, pointing directly in the longitudinal direction of the catheter, or be slightly curved, so that the end of the tip points in a direction which is non-parallel to the longitudinal direction of the catheter. Further, many different materials and material combinations may be used to produce the tubular shaft, and still obtain the desired material properties. Such and other modifications should be construed to fall within the scope of the appended claims.

The invention claimed is:

1. A urinary catheter comprising a tubular shaft extending between an insertion end and a discharge end, wherein the insertion end has a closed forward end and wherein the tubular shaft has a single internal lumen, the tubular shaft being formed of at least two materials having different properties, each of said materials being arranged substantially separated from each other in distinct zones, at least one of said distinct zones extending over essentially the entire length of the tubular shaft, wherein at least one of a width or thickness of said zones varies over the length of the tubular shaft, to form two or more uniform sections of the tubular shaft having various relative amounts of said materials, and wherein at least one transition between two such uniform sections is formed by at least one transition section providing a gradual transition between said uniform sections, and wherein the tubular shaft has an essentially constant outer diameter along substantially the entire length of the tubular shaft and essentially constant inner diameter along the entire internal lumen, wherein the catheter tube comprises a circular wall surrounding the internal lumen, and wherein the circular wall has a uniform and constant wall thickness around the circumference and over substantially the entire length of the tubular shaft.

2. The urinary catheter of claim 1, wherein each transition section has an extension within the range of 2-30% of the total length of the tubular shaft.

3. The urinary catheter of claim 1, wherein each transition section has an extension within the range of 4-20% of the total length of the tubular shaft.

4. The urinary catheter of claim 1, wherein each transition section has an extension within the range of 5-10% of the total length of the tubular shaft.

5. The urinary catheter of claim 1, wherein the two or more uniform sections in total extend over at least 50% of the total length of the tubular shaft.

6. The urinary catheter of claim 1, wherein the two or more uniform sections in total extend over at least 75% of the total length of the tubular shaft.

7. The urinary catheter of claim 1, wherein the two or more uniform sections in total extend over at least 90% of the total length of the tubular shaft.

8. The urinary catheter of claim 1, wherein the two materials have different hardness, one being softer and one being more rigid, thereby providing uniform sections having different flexibility.

9. The urinary catheter of claim 1, wherein the tubular shaft is an extruded tube formed by intermittent extrusion using two or more materials.

10. The urinary catheter of claim 1, wherein all of said at least two distinct zones extend continuously over essentially the entire length of the tubular shaft.

11. The urinary catheter of claim 1, wherein the distinct zones of different materials extend in a longitudinal direction of the catheter, are separated in a circumferential direction, and the zones have varying width in the circumferential direction along the length of the catheter.

12. The urinary catheter of claim 1, wherein the distinct zones of different materials extend in a longitudinal direction of the catheter, are separated in layers, and the layers have varying thickness along the length of the catheter.

13. The urinary catheter of claim 12, wherein each layer extends around the entire circumference of the catheter.

14. The urinary catheter of claim 1, wherein the tubular shaft comprises a uniform section being closest to the insertion end which is softer than another section being farther away from the insertion end.

15. The urinary catheter of claim 14, wherein an additional softer uniform section is arranged in the vicinity of the middle of the catheter shaft or the middle of an insertable part of the catheter shaft.

16. The urinary catheter of claim 1, wherein the tubular shaft comprises at least four uniform sections, at least two being relatively softer and at least two being relatively stiffer, the softer and stiffer sections being arranged in an alternating fashion along the length of the catheter shaft, and with transition sections being arranged between all adjacent uniform sections.

17. The urinary catheter of claim 1, wherein the zones are visibly discernible from each other, thereby providing markings related to at least one of a rotational position of the catheter and a length position along the catheter shaft.

18. The urinary catheter of claim 1, wherein at least one of said uniform sections has is relatively softer, and has a bending stiffness in the range of 25-150 MPa*mm$^4$, and another of said uniform sections is relatively stiffer, and has a bending stiffness in the range of 180-1600 MPa*mm$^4$.

19. The urinary catheter of claim 18, wherein the another of said uniform sections has a bending stiffness in the range 300-1500 MPa*mm$^4$.

20. The urinary catheter of claim 1, wherein the tubular shaft is at least partly coated with a hydrophilic surface coating, the coating covering at least an insertable part of the catheter, said hydrophilic surface coating exhibiting a low friction when wetted.

* * * * *